US 6,656,453 B2
Dec. 2, 2003

(54) MEDICAMENTS

(75) Inventors: Michael Thomas Riebe, Raleigh, NC (US); Sarvajna Kumar Dwivedi, San Diego, CA (US); Li Li-Bovet, Scotch Plains, NJ (US)

(73) Assignee: SmithKline Beecham Corporation, Philadelphia, PA (US)

(*) Notice: Subject to any disclaimer, the term of this patent is extended or adjusted under 35 U.S.C. 154(b) by 19 days.

This patent is subject to a terminal disclaimer.

(21) Appl. No.: 10/185,193

(22) Filed: Jun. 27, 2002

(65) Prior Publication Data

US 2002/0176824 A1 Nov. 28, 2002

Related U.S. Application Data

(63) Continuation of application No. 09/091,496, filed as application No. PCT/GB96/03154 on Dec. 19, 1996, now Pat. No. 6,558,651.

(30) Foreign Application Priority Data

Dec. 22, 1995 (GB) .............................................. 9526392

(51) Int. Cl.$^7$ .............................. A61K 9/12; A61K 9/14
(52) U.S. Cl. .......................... 424/45; 424/46; 424/489; 424/499; 514/630
(58) Field of Search ...................... 424/45, 46, 489, 424/499; 514/630

(56) References Cited

U.S. PATENT DOCUMENTS

| 3,987,192 A | 10/1976 | Wright |
| 4,405,598 A | 9/1983 | Brown |
| 4,476,130 A | 10/1984 | Wade |
| 5,118,494 A | 6/1992 | Schultz et al. |
| 5,126,123 A | 6/1992 | Johnson |
| 5,225,183 A | 7/1993 | Purewal et al. |
| 5,348,730 A | 9/1994 | Greenleaf et al. |
| 5,376,386 A | 12/1994 | Ganderton et al. |
| 5,562,923 A | 10/1996 | Trofast et al. |
| 5,637,620 A | 6/1997 | Trofast et al. |
| 5,709,884 A | 1/1998 | Trofast et al. |
| 5,736,124 A | 4/1998 | Akehurst et al. |
| 5,874,063 A | 2/1999 | Briggner et al. |
| 6,131,566 A | 10/2000 | Ashurst et al. |
| 6,143,277 A | 11/2000 | Ashurst et al. |
| 6,149,892 A | 11/2000 | Britto |

FOREIGN PATENT DOCUMENTS

| EP | 0 372 777 | 6/1990 |
| EP | 0 504 112 | 9/1992 |
| EP | 0 508 969 | 10/1992 |
| EP | 0 680 752 | 11/1995 |
| WO | 84 00294 | 2/1984 |
| WO | 91 04011 | 4/1991 |
| WO | 91 11173 | 8/1991 |

(List continued on next page.)

OTHER PUBLICATIONS

U.S. patent application Ser. No. 09/952,811, filed Sep. 14, 2001.

Primary Examiner—Michael G. Hartley
Assistant Examiner—Mina Haghighatian
(74) Attorney, Agent, or Firm—Robert J. Smith

(57) ABSTRACT

This invention relates to aerosol formulations of use for the administration of medicaments by inhalation. More particularly, the invention relates to a pharmaceutical aerosol formulation which comprises particulate salbutamol sulphate having a crystalline form in which the outer layer of the crystals is substantially non-amorphous; and 1,1,1,2-tetrafluoroethane. A method of treating respiratory disorders which comprises administration by inhalation of an effective amount of a pharmaceutical aerosol formulation as defined is also described.

16 Claims, 2 Drawing Sheets

FOREIGN PATENT DOCUMENTS

Figure 1:
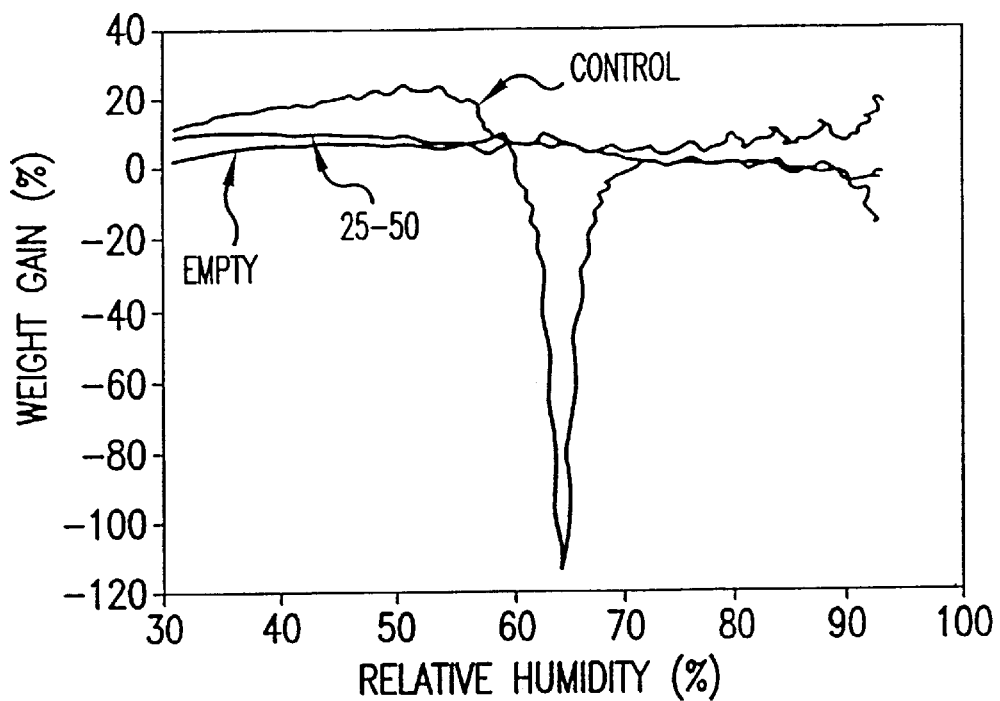

| WO | 91 16882 | 11/1991 |
|----|----------|---------|
| WO | 92 00107 | 1/1992  |
| WO | 92 08446 | 5/1992  |
| WO | 92 18110 | 10/1992 |
| WO | 92 22287 | 12/1992 |
| WO | 93 11743 | 6/1993  |
| WO | 93 11745 | 6/1993  |
| WO | 93 11747 | 6/1993  |
| WO | 93 18746 | 9/1993  |
| WO | 95 05805 | 3/1995  |

MEDICAMENTS

CROSS-REFERENCE TO RELATED APPLICATIONS

This application is a continuation application of Ser. No. 09/091,496 filed Jun. 18, 1998, now U.S. Pat. No. 6,558,651 allowed, which was filed pursuant to 35 U.S.C. §371 as a United States National Phase Application of International Application No. PCT/GB96/03154 filed Dec. 19, 1996 which claims priority from GB Application No. 9526392.7 filed Dec. 22, 1995, the disclosures of which are incorporated herein by reference in their entirety.

FIELD AND BACKGROUND OF THE INVENTION

This invention relates to aerosol formulations of use for the administration of medicaments by inhalation. More particularly, the invention relates to aerosol formulations comprising a fluorocarbon or hydrogen-containing chlorofluorocarbon propellant.

Drugs for treating respiratory and nasal disorders are frequently administered in aerosol formulations through the mouth or nose. One widely used method for dispensing such aerosol drug formulations involves making a suspension formulation of the drug as a finely divided powder in a liquefied gas known as a propellant. The suspension is stored in a sealed container capable of withstanding the pressure required to maintain the propellant as a liquid. The suspension is dispensed by activation of a dose metering valve affixed to the container. Devices used for dispensing drugs in this way are known as "metered dose inhalers" (MDI's). See Peter Byron, *Respiratory Drug Delivery*, CRC Press, Boca Raton, Fla. (1990) for a general background on this form of therapy.

Patients often rely on medication delivered by MDI's for rapid treatment of respiratory disorders which are debilitating and in some cases, even life threatening. Therefore, it is essential that the prescribed dose of aerosol medication delivered to the patient consistently meet the specifications claimed by the manufacturer and comply with the requirements of regulatory authorities. That is, every dose in the can must be the same within close tolerances.

Some aerosol drugs tend to adhere to the inner surfaces, i.e. walls, valves, and caps, of the MDI. This can lead to the patient getting significantly less than the prescribed amount of drug upon each activation of the MDI. The problem has been observed particularly in relation to formulations comprising salbutamol sulphate and hydrofluoroalkane (also known as simply "fluorocarbon") propellant systems, for example 1,1,1,2-tetrafluoroethane, under development in recent years to replace conventional chloroflurocarbon propellants.

SUMMARY OF THE INVENTION

We have found that using a recrystallised form of salbutamol sulphate, can reduce or eliminate the problem of drug adhesion or deposition and thus ensures consistent delivery of medicament from the metered dose inhaler.

Accordingly, there is provided in one aspect of the invention a pharmaceutical aerosol formulation which comprises particulate salbutamol sulphate having a crystalline form in which the outer layer of the crystals is substantially non-amorphous; and 1,1,1,2-tetrafluorethane.

In a further aspect of the invention, there is provided a pharmaceutical aerosol formulation which comprises particulate salbutamol sulphate having a water content of less than about 0.4% by weight; and 1,1,1,2-tetrafluoroethane.

In another aspect of the present invention, there is provided a pharmaceutical aerosol formulation which comprises particulate salbutamol sulphate having substantially no thermal activity as measured by microcalorimetry at about 25° C. and between about 30% to about 90% relative humidity; and 1,1,1,2-tetrafluoroethane.

In yet another aspect of the present invention, there is provided a pharmaceutical aerosol formulation which comprises particulate salbutamol sulphate having reduced thermal activity substantially as shown in FIG. 1; and 1,1,1,2-tetrafluorethane.

DETAILED DESCRIPTION OF THE PREFERRED EMBODIMENTS

The salbutamol sulphate used in the formulations of the present invention hereinafter referred to as 'annealed' salbutamol sulphate can suitably be prepared by subjecting particulate salbutamol sulphate to a temperature of between 0° C. to about 100° C. with a relative humidity of between about 20% to about 90%. Alternatively, the salbutamol sulphate can be prepared by subjecting particulate sulphate to elevated temperatures, such as about 40° C. to about 100° C. under vacuum.

Whilst not being bound by theory, treating the salbutamol sulphate in either of the above ways is believed to recrystallise a layer of high energy or amorphous material on the drug surface to provide a stable, relatively low energy ie, lacks significant thermal activity, crystalline form which has a reduced water content typically of less than about 0.4% by weight, referred to as 'annealed' salbutamol sulphate. Preferably the salbutamol sulphate employed in the formulations of the present invention will have a water content of less than about 0.35% by weight and more preferably less than about 0.3% by weight Particulate salbutamol sulphate, as described in U.S. Pat. No. 5,225,183, which has not been so treated has significantly greater thermal activity and a higher water content normally of about 0.5% by weight or more.

Thus, there is provided in a further aspect of the present invention a pharmaceutical aerosol formulation which comprises
(a) particulate salbutamol sulphate obtainable by subjecting said particulate salbutamol sulphate to a temperature of between about 0° C. to about 100° C. with a relative humidity of between about 20% to about 90%; and
(b) 1,1,1,2-tetrafluoroethane.

In yet a further aspect of the present invention, there is provided a pharmaceutical aerosol formulation which comprises
(a) particulate salbutamol sulphate obtainable by subjecting said particulate salbutamol to elevated temperatures under vacuum: and
(b) 1,1,1,2-tetrafluoroethane.

Whilst the desired particulate form of salbutamol sulphate (that is substantially non-amorphous, reduced water content or substantially no thermal activity) has been prepared by the methods described herein, it will be appreciated that other methods which give salbutamol sulphate having said desired characteristics may also be used.

Preferably the annealed salbutamol sulphate employed in the aerosol Formulations of the present invention is obtainable by subjecting the particulate salbutamol sulphate to a temperature of about 10° C. to 500° C. with a relative humidity of about 55% to about 65%. A temperature of about 20° C. to 30° C., for example 25° C., with a relative humidity of about 60% is particularly preferred.

Alternatively, the annealed salbutamol sulphate can be obtained by elevated temperatures such as between about 40° C. to about 100° C., preferably greater than about 60° C., especially greater than about 80° C.

The time required for treating the salbutamol sulphate will naturally depend upon the amount of drug to be treated, the way in which it is presented, and the temperature and/or relative humidity selected. Thus, the time required may be from hour(s) to day(s). At lower humidities and/or where lower temperatures are used, the time required may be longer, for example, one or more weeks. For manufacturing purposes, shorter treatment times, for example of 1 to 5 hours, are preferred.

To ensure that the micronised salbutamol sulphate is substantially uniformly annealed, particularly when large quantities of drug are to be treated, the drug may advantageously be presented such that the surface area of drug in contact with the humid and/or warm air is maximised. For example, a quantity of drug may be presented in an open tray the base of which comprises a plurality of small apertures to permit access of the humid and/or warm air to the salbutamol sulphate.

The particle size of the particulate (e.g. micronised) salbutamol sulphate should be such as to permit inhalation of substantially all of the medicament into the lungs upon administration of the aerosol formulation and thus will be less than 100 microns, desirably less than 20 microns, and preferably in the range of 1 to 10 microns, for example 1 to 5 microns.

The final aerosol formulation desirably contains 0.005 to 10% w/w, preferably 0.005 to 5% w/w, especially 0.01 to 1% w/w of salbutamol sulphate relative to the total weight of the formulation. Particularly preferred are formulations containing 0.05–0.2% w/w of salbutamol sulphate relative to the total weight of the formulation.

The final aerosol formulation may also include one or more adjuvants typically used in pharmaceutical aerosol formulations. The term 'adjuvants' as used herein means additives having little or no pharmacological activity (for the quantities used) but which enhance the drug formulation or the performance of the MDI.

Such adjuvants include alcohols, alkanes, dimethyl ether, surfactants (including fluorinated and non-fluorinated surfactants) carboxylic acids, polyethoxylates and carriers such as sugars, particularly lactose.

Preferred formulations contain an alcohol and/or a surfactant and/or a sugar.

An alcohol particularly ethanol may be included in the aerosol formulation, preferably in an amount of 0.01% to 15% w/w, especially 0.01% to 5% w/w based on propellant.

Sugars such as lactose may be incorporated in the formulation of the present invention, preferably in an amount of 0.0001 to 50% w/w, more preferably 0.001 to 20%, for example 0.001 to 1% w/w based on the total weight of the formulation. Generally, the ratio of salbutamol sulphate:sugar falls within the range of 1:0.001 to 1:100 preferably 1:0.1 to 1:10. Other sugars which may be used in the formulations include, for example, sucrose and dextrose. Lactose is, however, preferred.

Surfactants which may desirably be incorporated in the formulation of the present invention include both non-fluorinated and fluorinated surfactants known in the art, for example, in U.S. Pat. No. 4,352,789, EP0478686 and WO92/00107. Examples of suitable surfactants include oils, derived from natural sources, sorbitan trioleate available under the trade name Span 85, lecithins derived from natural sources such as those available under the trade name Epikuron, particularly Epikuron 200, synthetic lecithin, oleic acid, cetyl alcohol and stearyl alcohol.

The surfactants are generally present in amounts not exceeding 5% by weight of the total formulation. They will usually be present in the weight ratio of 1:100 to 10:1 surfactant:salbutamol sulphate, but the surfactant may exceed this weight ratio in cases where the salbutamol sulphate concentration in the formulation is very low.

Particularly preferred formulations of the present invention, however, are those which are substantially free of surfactant. By 'substantially-free of surfactant' is meant formulations which contain no significant amounts of surfactant ie a non-functional amount, for example less than 0.0001% by weight of medicament.

Thus, formulations consisting essentially of or consisting of annealed salbutamol sulphate and 1,1,1,2-tetrafluoroethane form yet a further aspect of the present invention.

It will be appreciated by those skilled in the art that the aerosol formulations according to the invention may, if desired, contain a combination of two or more active ingredients. Accordingly the present invention further provides aerosol formulations in accordance with the invention which contain one or more particulate medicaments in addition to salbutamol sulphate. Medicaments may be selected from any suitable drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; antiinflammatories, e.g. fluticasone, beclomethasone, flunisolide, budesonide, tipredane or triamcinolone acetonide; antitussives, e.g. noscapine; diuretics, e.g. amiloride; anticholinergics e.g. ipratropium, atropine or oxitropium; hormones, e.g. cortisone, hydrocortisone or prednisolone; xanthines e.g. aminophylline, chorine theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred aerosol formulations contain salbutamol sulphate in combination with an antiinflammatory steroid such as a beclomethasone ester (e.g. the dipropionate) or a fluticasone ester (e.g. the propionate) or an antiallergic such as cromoglycate (e.g. the sodium salt). Combinations of salbutamol sulphate and fluticasone propionate or beclomethasone dipropionate are preferred.

If desirable and appropriate the adjuvants and additional medicaments can be treated in a similar manner to salbutamol sulphate. That is each additional adjuvant or medicament can be treated at different temperature/relative humidity combinations as required. Alternatively, the salbutamol sulphate can be admixed with the desired adjuvant and/or medicament and then treated prior to incorporation in the aerosol formulation.

The formulations of the invention may be prepared by dispersal of the annealed salbutamol sulphate in the selected propellant in an appropriate container, e.g. with the aid of sonication. The process is desirably carried out under anhydrous conditions to obviate any adverse effects of moisture on suspension stability.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The particle size distribution of the aerosol formulations according to the invention is particularly impressive and may be measured by conventional techniques, for example by cascade impaction or by the "twin Impinger" analytical process. As used herein reference to the "twin Impinger" assay means "Determination of the deposition of the emitted dose in pressurised inhalations using apparatus A" as defined in British Pharmacopaeia 1988, pages A204–207, Appendix XVII C. Such techniques enable the "respirable fraction" of the aerosol formulations to be calculated. As used herein reference to "respirable fraction" means the amount of active ingredient collected in the lower impingement chamber per actuation expressed as a percentage of the total amount of active ingredient delivered per actuation using the twin impinger method described above. The formulations according to the invention have been found to have a respirable fraction of 20% or more by weight of the medicament, preferably 25 to 70%, for example 30 to 60%.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve.

Aluminium cans which have their inner surfaces coated with a fluorocarbon polymer are particularly preferred. Such polymers can be made of multiples of the following monomeric units: tetrafluoroethylene (PTFE), fluorinated ethylene propylene (FEP), perfluoroalkoxyalkane (PFA), ethylene tetrafluoroethylene (EFTE), vinyldienefluoride (PVDF), and chlorinated ethylene tetrafluoroethylene. The use of such polymer-coated cans can help to reduce even further the deposition or adhesion of salbutamol sulphate on the inner surfaces of the can.

The MDI can may be coated by means known in the art of metal coating. For example, a metal such as aluminium or stainless steel may be precoated as coil stock and cured before being stamped or drawn into the can shape. Further techniques include spraying the inside of preformed MDI cans with the polymer, dipping preformed cans into the polymer and pouring the polymer inside the MDI cans, followed by curing. Alternatively, the fluorocarbon polymer may be formed in situ using plasma polymerisation of the fluorocarbon monomers. Fluorocarbonpolymer films may be blown inside the MDI cans to form bags. A variety of fluorocarbon polymers such as ETFE, FEP, and PTFE are available as film stock.

The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak pic, UK (e.g. BK300, BK356) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The annealed salbutamol sulphate is added to a charge vessel and liquefied propellant is pressure filled through the charge vessel into a manufacturing vessel. The drug suspension is mixed before recirculation to a filling machine and an aliquot of the drug suspension is then filled through the metering valve into the canister. Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

Suitable daily doses, may be, for example in the of 100 to 1000 microgram of salbutamol sulphate depending on the severity of the disease.

Thus, for example, each valve actuation may deliver 100 microgram salbutamol sulphate. Typically each filled canister for use in a metered dose inhaler contains 100, 160 or 240 metered doses or puffs of medicament.

The filled canisters and metered dose inhalers described herein comprise further aspects of the present invention.

A still further aspect of the present invention comprises a method of treating respiratory disorders such as, for example, asthma, which comprises administration by inhalation of an effective amount of a formulation as herein described.

The invention is further illustrated but not limited by the following examples.

EXAMPLE 1

Micronised salbutamol sulphate (450 g, 2 cm depth) was treated at a temperature of 25° C. at a relative humidity of 60% for 65 hours. The salbutamol sulphate was stirred once every 24 hours to enhance exposure to moist air.

To confirm that the salbutamol sulphate had been converted to the desired low energy, crystalline form i.e. had been annealed, the thermal activity and the water content of the treated salbutamol sulphate compared to untreated salbutamol sulphate was measured using standard microcalorimetry techniques and moisture sorption techniques respectively.

Thermal Activity

A Hart Scientific Microcalorimeter (model 4400) was operated at 25° C. with a water adsorption unit and scanned from about 30% to about 90% relative humidity over a 11.5 hour period. Thermal equilibration time was 1 to 2 hours.

As shown in FIG. 1, the untreated salbutamol sulphate showed an exothermic rise in heat rate up to approximately 55% relative humidity followed by a large endothermic response. This thermal activity was absent in the treated salbutamol sulphate, demonstrating that annealing had occurred.

Water Content

A VTI Corp vacuum balance moisture sorption apparatus (model MB300G) was operated at 25° C., and scanned from about 20% to about 90% relative humidity, total scan time about 15 hours. Drying was accomplished at 35° C. under vacuum for approximately 1 hour before the equilibrium condition used for the scans of 3 micrograms/6 minutes was achieved. This same equilibrium weight change criterion was used for the sorption measurements.

Figure 2:
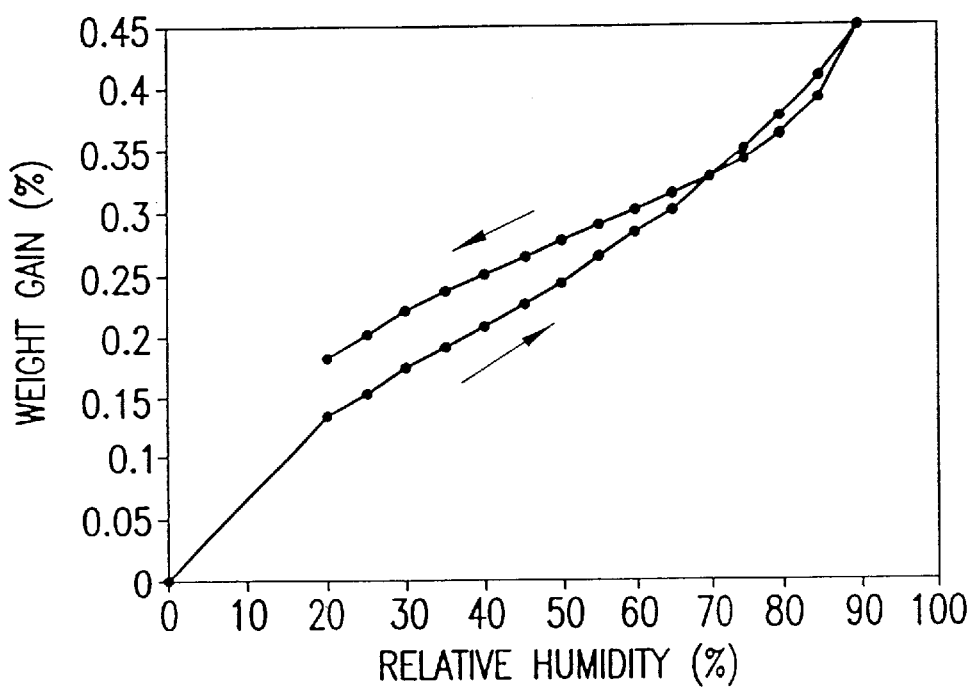
Figure 3:
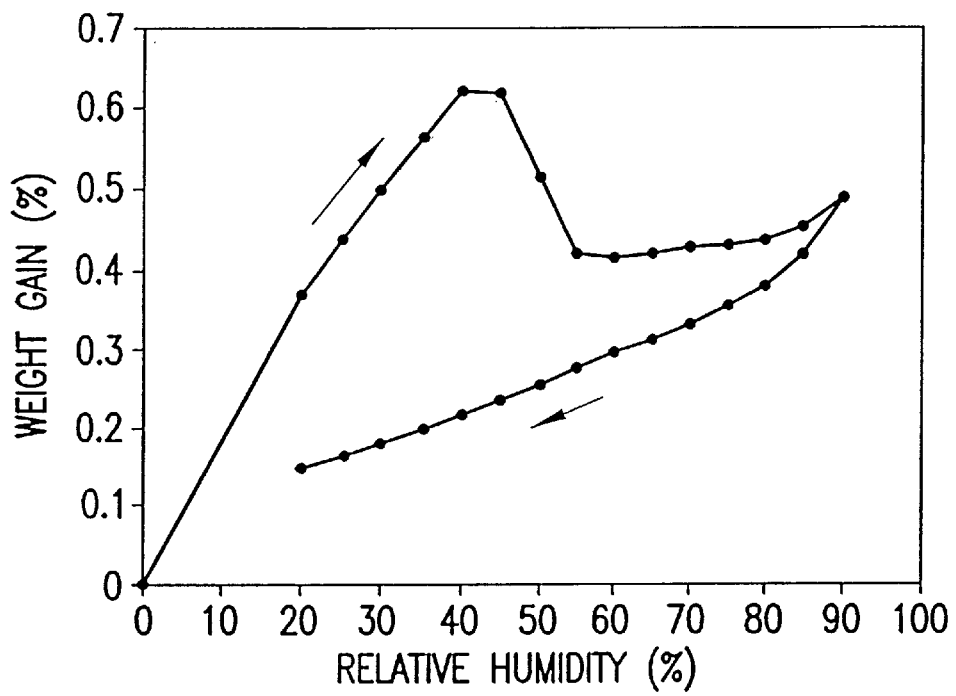

FIGS. 2 and 3 show the moisture sorption profiles of treated ie annealed and untreated salbutamol sulphate respectively. The figures plot the % weight gain (normalised by the dry weight) against relative humidity at 25° C. The untreated salbutamol sulphate exhibits a significantly larger moisture content compared with the treated salbutamol sulphate, clearly demonstrating that annealing had occurred.

Formulation

Annealed salbutamol sulphate (31.8 mg) was added to 1,1,1,2-tetrafluoroethane (19.8 g) in an aluminium alloy canister and the canister fitted onto a plastic actuator containing the atomising nozzle to complete the MDI.

Dose delivery from the MDI was tested under simulated use conditions and was found to be constant compared to control MDIs containing untreated salbutamol sulphate which exhibit a significant decrease in dose delivered through use.

EXAMPLES 2 and 3

Two 7 g batches of salbutamol sulphate were subjected to a temperature of 25° C. at 85% relative humidity (Example 2) and a temperature of 40° C. at 85% relative humidity (Example 3) for 24 hours.

Figure 4:
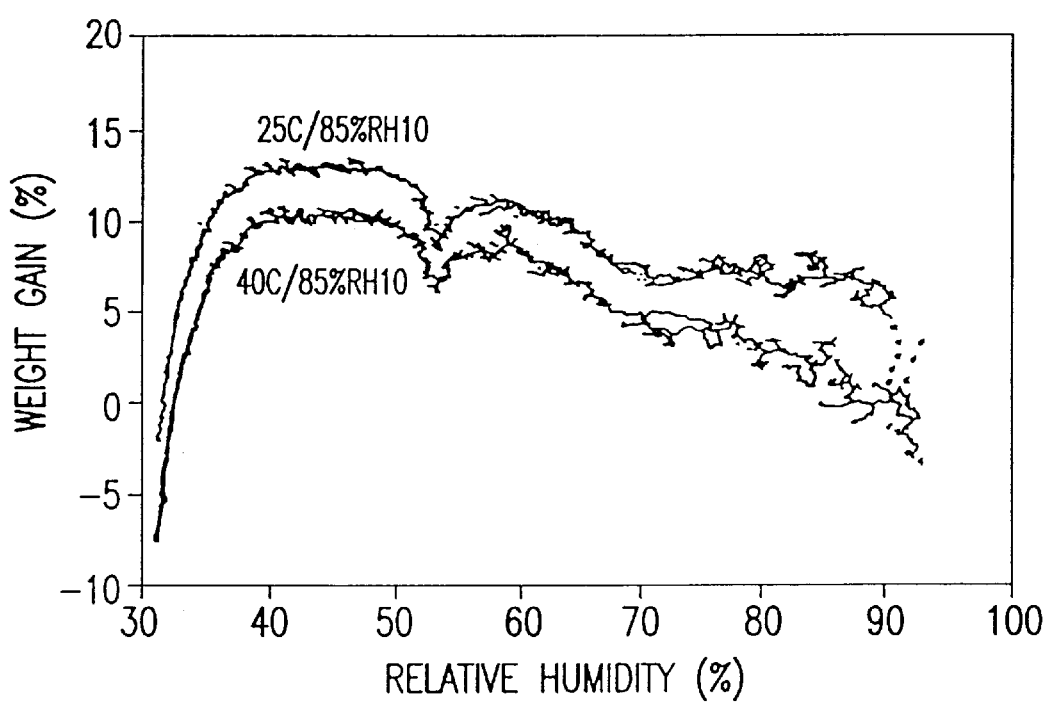

The thermal activity of the salbutamol sulphate was measured as described in Example 1. The microcalorimetry results are shown in FIG. 4. FIG. 4 shows that both batches of salbutamol sulphate lack significant thermal activity demonstrating that annealing had occurred.

Annealed salbutamol sulphate (31.8 mg or 15.42 mg) is added to 1,1,1,2-tetrafluorethane (19.8 g or 9.6 g respectively) in an aluminium alloy canister as described in Example 1.

EXAMPLE 4

Micronised salbutamol sulphate (2.2 Kg) is subjected to a temperature of 25° C. at a relative humidity of 60% for about 1.5 hours.

Thermal activity of the salbutamol sulphate is measured as described in Example 1. The microcalorimetry data shows that the salbutamol sulphate lacks significant thermal activity demonstrating that annealing has occurred.

Annealed salbutamol sulphate (31.8 mg or 15.42 mg) is added to 1,1,1,2-tetrafluoroethane (19.8 g or 9.6 g respectively) in an aluminium alloy canister which has its inner surfaces coated with a fluorocarbon polymer.

Dose Delivery from the MDIs are tested under simulated use conditions and are found to be constant compared to control MDIs containing untreated salbutamol sulphate which exhibit a significant decrease in dose delivered through use.

It will be appreciated that modifications to the formulation and the methods described herein can be readily made by a person skilled in the art without departing from the scope of the present invention. Protection is sought for all subject matter described herein including any such modifications.

What is claimed is:

1. A process of forming a pharmaceutical aerosol formulation, said process consisting essentially of:
    subjecting particulate salbutamol sulphate to a temperature between about 0° C. and about 100° C. with a relative humidity of between about 20% to about 90% to form annealed particulate salbutamol sulphate; and
    combining the annealed salbutamol sulphate with a propellant comprising 1,1,1,2-tetrafluoroethane to form a pharmaceutical aerosol formulation.

2. The process according to claim 1, wherein said step of subjecting particulate salbutamol sulphate to a temperature of between about 0° C. and about 100° C. with a relative humidity of between about 20% to about 90% comprises subjecting particulate salbutamol sulphate to a temperature of between about 10° C. and about 50° C. with a relative humidity of between about 55% to about 65%.

3. The process according to claim 1, wherein said step of subjecting particulate salbutamol sulphate to a temperature of between about 0° C. and about 100° C. with a relative humidity of between about 20% to about 90% comprises subjecting particulate salbutamol sulphate to a temperature of between about 20° C. and about 30° C. with a relative humidity of about 60%.

4. The process according to claim 1, wherein the annealed particulate salbutamol sulphate is present in the pharmaceutical aerosol formulation in an amount from about 0.01 to about 1% w/w.

5. The process according to claim 1, wherein the annealed particulate salbutamol sulphate is present in the pharmaceutical aerosol formulation an amount ranging from about 0.05 to about 0.2% w/w.

6. The process according to claim 1, the pharmaceutical aerosol formulation consisting essentially of the annealed particulate salbutamol sulphate and 1,1,1,2-tetrafluoroethane as propellant.

7. The process according to claim 1, wherein the annealed particulate salbutamol sulphate is substantially thermally inactive as measured by microcalorimetry at about 25° C. and between about 30% to about 90% relative humidity.

8. The process according to claim 7, wherein the annealed particulate salbutamol sulphate is micronized and includes a recrystallized outer layer.

9. A process of forming a pharmaceutical aerosol formulation, said process consisting essentially of:

subjecting particulate salbutamol sulphate to elevated temperatures under vacuum to form annealed particulate salbutamol sulpahte; and combining the annealed salbutamol sulphate with a propellant comprising 1,1,1,2-tetrafluoroethane to form a pharmaceutical aerosol formulation.

10. The process according to claim 9, wherein said step of subjecting particulate salbutamol sulphate to elevated temperatures under vacuum to form annealed particulate salbutamol sulphate comprises subjecting particulate salbutamol sulphate to a temperature of from about 40° C. to about 100° C.

11. The process according to claim 9, wherein said step of subjecting particulate salbutamol sulphate to elevated temperatures under vacuum to form annealed particulate salbutamol sulphate comprises subjecting particulate salbutamol sulphate to a temperature greater than about 60° C.

12. The process according to claim 9, wherein the annealed particulate salbutamol sulphate is present in the pharmaceutical aerosol formulation in an amount from about 0.01 to about 1% w/w.

13. The process according to claim 9, wherein the annealed particulate salbutamol sulphate is present in the pharmaceutical aerosol formulation an amount ranging from about 0.05 to about 0.2% w/w.

14. The process according to claim 9, the pharmaceutical aerosol formulation consisting essentially of the annealed particulate salbutamol sulphate and 1,1,1,2-tetrafluoroethane as propellant.

15. The process according to claim 9, wherein the annealed particulate salbutamol sulphate is substantially thermally inactive as measured by microcalorimetry at about 25° C. and between about 30% to about 90% relative humidity.

16. The process according to claim 15, wherein the annealed particulate salbutamol sulphate is micronized and includes a recrystallized outer layer.

* * * * *